United States Patent [19]

Park et al.

[11] Patent Number: 5,221,800
[45] Date of Patent: Jun. 22, 1993

[54] ONE STEP AIR OXIDATION OF CYCLOHEXANE TO PRODUCE ADIPIC ACID

[75] Inventors: Chang-Man Park, Naperville, Ill.; Nancy S. Goroff, West Los Angeles, Calif.

[73] Assignee: Amoco Corporation, Chicago, Ill.

[21] Appl. No.: 875,993

[22] Filed: Apr. 29, 1992

Related U.S. Application Data

[63] Continuation of Ser. No. 739,692, Aug. 2, 1991, abandoned, which is a continuation-in-part of Ser. No. 655,081, Feb. 14, 1991, abandoned, which is a continuation of Ser. No. 402,614, Sep. 5, 1989, abandoned.

[51] Int. Cl.$^5$ ............................................. C07C 51/31
[52] U.S. Cl. ................................................... 562/543
[58] Field of Search ......................................... 562/543

[56] References Cited

U.S. PATENT DOCUMENTS 4,263,453  4/1981  Schutz ................................. 562/543

Primary Examiner—José G. Dees
Assistant Examiner—Joseph M. Conrad, III
Attorney, Agent, or Firm—Thomas E. Nemo; Wallace L. Oliver; Frank J. Sroka

[57] ABSTRACT

A process for the manufacture of adipic acid is disclosed. In this process, cyclohexane is oxidized in an aliphatic monobasic acid solvent in the presence of a soluble cobalt salt wherein water is continuously or intermittently added to the reaction system after the initiation of oxidation of cyclohexane as indicated by a suitable means of detection, and wherein the reaction is conducted at a temperature of about 50° C. to about 150° C. at an oxygen partial pressure of about 50 to about 420 pounds per square inch absolute.

16 Claims, No Drawings

ONE STEP AIR OXIDATION OF CYCLOHEXANE TO PRODUCE ADIPIC ACID

This is a continuation of application Ser. No. 07/739,692, filed Aug. 2, 1991, now abandoned, which in turn is a continuation-in-part of Ser. No. 07/655,081, now abandoned, filed Feb. 14, 1991, which is a continuation of Ser. No. 07/402,614, filed Sep. 5, 1989, now abandoned.

FIELD OF THE INVENTION

This invention relates to a process of converting cyclohexane to adipic acid in high yield which comprises oxidizing cyclohexane with a source of oxygen to adipic acid in the presence of water and monobasic acid solvent. The catalyst for this reaction is an active form of cobalt, considered to be the cobaltic ion.

BACKGROUND OF THE INVENTION

Adipic acid is a large volume commodity chemical used for the production of polymeric compounds. Cyclohexane can be used as a precursor for the manufacture of adipic acid. Of the 688,000 tons/year adipic acid capacity in the United States in 1978, 677,000 tons/year, 98%, was based on cyclohexane feedstock, Kirk-Othmer, *Ency. Chem. Tech.*, Vol. 1, 510, John Wiley & Sons, N.Y., 1978. Because of the large volume of adipic acid required for production of polymers, increases in adipic acid yields from precursors such as cyclohexane are of significant economic importance.

Processes for the preparation of adipic acid from cyclohexane using cobalt as a catalyst are taught by U.S. Pat. No. 4,032,569; U.S. Pat. No. 4,263,453 and Japanese Pat. No. 51075018. U.S. Pat. No. 4,032,569 to Onopchenko, et al. teaches that significantly higher conversions of cyclohexane to a product predominating in adipic acid is obtained if critical amounts of cobalt are present in the reaction zone, the temperature and pressure during the reaction are maintained within critical ranges and, if the reaction is terminated within a critical time period. Critical requirements are that at least about 25 millimols of cobalt be present per mole of cyclohexane in the process and that temperature be in the range of from about 85° C. to about 105° C., oxygen partial pressure at least about 150 psia for a period of about 0.5 to about 3 hours. Schultz, et al., U.S. Pat. No. 4,263,453 teaches the oxidation of cyclohexane in the presence of a cobalt catalyst wherein cobalt must be present in the form of its cobaltic ion. Schulz '453 teaches that the source of the cobaltic ion is immaterial as long as the cobaltic ions are maintained in the reaction mixture during the reaction period. In order to attain high conversion, the amount of cobalt is critical and must be in excess of about 25 millimoles of cobalt per mol of cyclohexane, preferably in the range of about 50 to 100 millimols of cobalt per mol of cyclohexane Schulz '453 further notes.

As is well-known, in the oxidation of cyclohexane to adipic acid in the presence of a cobalt salt, any cobalt salt of an organic acid can be used, see U.S. Pat. No. 3,231,608 to Kollar. However, it is also well-known that if the cobaltous salt is selected as the catalyst of choice because of availability and/or solubility requirements, the cobaltous ion must be oxidized to the cobaltic ion before the reaction of the oxidation of cyclohexane to adipic acid can proceed. A period of induction therefore occurs before the period of oxidation. The induction period can be reduced by the addition of an initiator to the reaction mixture It is therefore essential that an initiator be present in the process to reduce the total process time.

Despite the considerable work performed in this area by experimenters, reported yields of adipic acid from cyclohexane have been lessened by the co-production of byproducts such as glutaric acid and succinic acid. Additionally, process times have been long, as long as 4 hours, see U.S. Pat. No. 3,231,608.

To increase the yield of adipic acid, Schulz, U.S. Pat. No. 4,263,453, teaches the reaction must be carried out in the presence of selected amounts of added free water, generally at least about 0.5 wt% of water, relative to the weight of the monobasic acid solvent, but generally no more than about 15 wt % of water relative to the solvent is taught as suitable. Reported yields of adipic acid range from 70.7 to 80.6%. Yield of glutaric acid ranges from 9.3 to 14.7%. Yield of succinic acid ranges from 9.4 to 13.9%. The water is introduced into the process at the beginning of the process, at the beginning of the period of induction. Total process time, including induction period and reaction period, is in the range of from 3.3 hours to 6.3 hours.

SUMMARY OF THE INVENTION

Significantly higher yields of adipic acid are obtained from cyclohexane utilizing this novel process which comprises adding water continuously or intermittently only after the initiation of the oxidation reaction of cyclohexane as indicated by the production of carbon oxides or absorption of oxygen or by a noticeable rise in reaction temperature, while employing cobalt as catalyst and an initiator comprising cyclohexanone or a mixture of cyclohexanone and cyclohexanol. During this process the amount of water added does not exceed 50 weight percent of cyclohexane feedstock. In the process, water is continuously or intermittently added only after the oxidation reaction begins. The components in the reaction are cyclohexane, an initiator, an aliphatic monobasic acid solvent, cobaltic ions, air and water. In an alternative embodiment the water can be added intermittently after the reaction has initated as indicated by the production of carbon oxides, the absorption of oxygen, or a noticeable rise in reaction temperature. Yields of adipic acid of 88 (mol) % are obtained.

DETAILS OF THE INVENTION

Suitable solvents are any aliphatic monobasic acid comprising primary and secondary hydrogen and having 2 to 8 carbon atoms, preferably having 2 to 4 carbon atoms. Examples of satisfactory monobasic acid solvents include acetic acid, propionic, normal butyric, capronic, pelagonic, trimethylacetic acid, etc. The preferred acid is acetic. The molar-ratio of the solvent to cyclohexane is between about 20 to 1 to about 1 to 1. The preferred range being about 10 to about 1. The cobalt catalyst is suitably present in its ionic form. The source of cobalt is immaterial as long as it is maintained as a cobaltic ion in the reaction mixture during the oxidation of cyclohexane to adipic acid. Thus, as a source thereof, any cobaltous or cobaltic salt of an organic acid can be employed, such as cobaltous or cobaltic acetate, propionate, naphthenate, etc. The amount of cobalt present in the reaction mixture is about 0.01 to 1 mol of cobalt per mol of cyclohexane. A cobaltous salt can be preferred because of commercial availability.

In the oxidation of cyclohexane with molecular oxygen and cobalt catalyst there is typically a period of induction before the oxidation reaction begins to proceed The induction period is well-known, and can be as long as 3 or 4 hours, or even longer It is therefore essential for economic reasons to reduce the induction period by means of the addition of an induction agent or initiator. It is also essential that an initiator be present during the oxidation of cyclohexane to adipic acid.

It has been found that the addition of water before or during the induction period appears to hinder the production of free radicals which typically would be generated by the presence of an initiator.

Cyclohexanone is preferred as an initiation agent. A mixture of cyclohexanone and cyclohexanol is conveniently used. Oxygen-containing aliphatic hydrocarbons such as acetaldehyde, methyl ethyl ketone, etc. are other initiation agents which can be effectively used. The amount of initiator can vary between about 0.1 to about 50 weight percent based on the cyclohexane feedstock, with preferred amounts of initiator being between about 0.3 to about 30 weight percent based on the cyclohexane.

Free molecular oxygen must also be present in the reaction zone to oxidize cyclohexane to adipic acid. Thus, either air or oxygen itself can be employed Another critical requirement herein in obtaining high conversions of cyclohexane to adipic acid is the partial pressure of oxygen over the reaction mixture. Accordingly, the oxygen partial pressure must be at least 50 pounds per square inch absolute, or even higher, but excellent conversions are obtained when the oxygen partial pressure is in the range of about 50 to about 420 pounds per square inch absolute Such pressures, moreover, are sufficient to maintain the reactants in the liquid phase. When the source of oxygen is air, the partial pressure of air is in the range of about 715 to about 2000 pounds per square inch absolute.

It has been found that increased yields of adipic acid, as much as 10% over yields taught in the prior art, can be obtained from oxidation of cyclohexane by addition of water either continuously or intermittently during the cyclohexane oxidation reaction in the presence of an initiator to generate free radicals It is essential, however, to add the water after the initiation of the oxidation reaction, as indicated, for example, by production of carbon oxides, to obtain a high yield of adipic acid and to reduce the production of by-products including glutaric and succinic acids. Any suitable means can be used to determine the initiation of the oxidation of cyclohexane to adipic acid, as indicated by the production of carbon oxides, or the absorption of oxygen or a rapid increase in the oxidation reaction to oxidize cyclohexane. Such means can include on-line measurement of carbon oxides in the oxidation reaction effluent or by monitoring an increase of the oxidation reaction temperature over the temperature at which the cyclohexane, initiator, catalyst and solvent, excluding any water, have been maintained in the reactor. Any other suitable means for detecting the onset of the oxidation Q reaction to oxidize cyclohexane to adipic acid can be utilized, such as measurement of the decrease in oxygen volume concentration in reactor effluent and thus the oxygen absorption. It is critical that the water be added to the oxidation reaction to oxidize cyclohexane to adipic acid after the onset of the oxidation of cyclohexane to adipic acid. It is believed that the continuous or intermittent addition of water improves the activity of the cobalt catalyst in the oxidation medium. In this novel process, yields of 88 mol percent are obtained The reaction temperature is critical and must be maintained in the range of about 50° to about 150° C, preferably in the range of about 60° to about 100° C. When temperatures in excess of the defined temperature ranges are employed there is an increasing tendency toward degradation of the desired adipic acid to glutaric and succinic acids. At very low temperatures the reaction tends to go to an exceedingly slow rate and would therefore be commercially unattractive. The reaction time is preferably short. Accordingly, it is preferred to use cyclohexanone or a mixture of cyclohexanone and cyclohexanol as an initiator to reduce the induction period by promoting the production of free radicals of cyclohexanone as an intermediate in the oxidation of the cyclohexane to adipic acid and improve the rate of oxygen absorption in the process of oxidizing cyclohexane to adipic acid. In this procedure the rate of reaction can be at a fast rate until no more cyclohexane can be converted. Of course, if desired, the reaction can be terminated at any selected time short of the time when oxygen absorption ceases. Thus, the reaction time can be as low as about 0.5 hours, for example, but usually conversion of cyclohexane, or absorption of oxygen, will cease when about 3 hours have elapsed. In general, the oxidation reaction time will be at least about 0.5 hour but no more than about 3-5 hours. The oxidation reaction times will obviously be in addition to the induction periods.

The reaction mixture is preferably well agitated to insure better contacting of the reactants. Agitation can be provided by mechanical stirring devices aided by the ebullition caused by the introduction of the oxygen-containing gas below the surface of the liquid reaction mixture.

At the end of the reaction period the reaction mixture can be separated into its component parts by any convenient means or known prior art. Thus, the contents of the reaction zone can be cooled to room temperature, depressurized and the reaction mixture withdrawn from the reaction zone. The reaction mixture is then diluted with an equal volume of water, and then heated on a steam bath to a temperature of about 80° C. for about one-half hour, or until the solution is pink, indicating the presence of cobaltous ions, and then evaporated to dryness. The residue is extracted with acetone to separate the organic products from the catalyst The organic products will contain the desired adipic acid and smaller amounts of glutaric and succinic acids The individual acids can be separated from each other in any conventional manner, for example, by crystallization from conventional solvents such as benzene or water. The catalyst will, at least in part, be present as the cobalt salt of adipic, glutaric and succinic acids To recover these acids from the catalyst, the catalyst is treated with sodium hydroxide to release the chemically-bound acids from the catalyst, at the same time converting the cobalt salt to its hydroxide or oxide state. Filtration will result in a solution containing the acids as their sodium salts. The latter are sprung with hydrochloric acid to form the desired free acids Recovery of these acids is effected by evaporating the solution to dryness and then extracting the residue with acetone to separate the acids from sodium chloride Evaporation of acetone will leave behind the additional adipic, glutaric and succinic acids. The catalyst can also be treated with concentrated hydrochloric acid and an evaporation to dryness will result in the formation of free organic acids and inorganic salts. These can readily be separated by extraction with a solvent, such as acetone mentioned above In a continuous oxidation procedure, the amount of product acids tied up with the cobalt will reach a steady-state concentration, and for practical reasons can be ignored in calculations as the catalyst is returned for recycle Analysis of Examples 1 to 8 indicates that conversion and selectivity of cyclohexane to adipic acid, and hence yield of adipic acid, is substantially and surprisingly increased by the process of the instant invention.

Examples 1 and 2 were performed in a semi-continuous mode. Examples 3 to 8 were performed in a batch mode.

Example 1, as a semi-continuous oxidation process, had an initial charge of acetic acid, glacial, of 420g and an additional 52.5g during the reaction Only 40g of cyclohexane had been added initially as feed to permit a greater yield initially, if possible, because of increased catalyst concentration initially. Yield of adipic acid was 76(wt)%, even with increased concentration of catalyst at the beginning of the oxidation reaction.

Analysis of Examples 1 and 2, comparing a straight cobalt catalyst system to a combined system of both cobalt and hydrobromic acid, is shown in Table I. The results of Example 2, as compared with Example 1, indicate that bromine actually interferes with the process, giving much less overall reactivity and more burning relative to the adipic acid produced The conversion and selectivity of Example 2 indicates that water has little effect on this system.

Examples 3, 4 and 5 indicate the effect manganese has Q on the oxidation reaction. Because cobalt suffers more deactivation in the presence of water than manganese does, a combined Co/Mn catalyst was tested to see how it compared to straight cobalt In Example 4, the same molar amount of catalyst was used as in the control, Example 3, but the catalyst was 90% manganese and only 10% cobalt As seen in Table II, almost no oxidation occurred in the manganese/cobalt system. In Example 5, a manganese/cobalt catalyst was again used, but sodium acetate was also added to the system. As shown again in Table II the acetate ion had no noticeable effect, and very little oxidation took place. This indicates that, although acetate ion may increase the activity of manganic ion, it either has no effect or can decrease the activity of manganous ion. From these examples, the data indicate that a straight cobalt catalyst is the best catalyst in the one-step oxidation system.

In Example 6, water was added after the reaction began, as indicated by a noticeably rise in temperature In Example 7, on the other hand, water was added 14 minutes after the reaction started, when the ratio of oxygen absorbed to cyclohexane present was calculated to be roughly 1:1.

As indicated by Examples 6 and 7, to obtain optimum yields, the water must be added after the reaction has been initiated. The water can be added continuously or intermittently. In Examples 6 and 7, water was added during the reaction, and 88 (mol)% yields were obtained However, Q in Example 1, wherein water was added as an initial charge, before the induction period, the yield was 76 (mol) %.

The examples given in Table III show the improvement in yield and selectivity for Examples 6 and 7 when compared to the control Example 1. Surprisingly, conversion increased when the water was added later. Conversion in Examples 6 and 7 was also greater than in Example 8, where no water was added, indicating that water frees the catalyst sites by dissociation. In Example 8 no water was added, and the yield was 80(mol) %.

We have discovered that adding water during the oxidation reaction increases yield, selectivity and conversion. The yield, selectivity and conversion significantly increase when water is added continuously or intermittently after the initiation of oxidation of cyclohexane than where water is added initially or not at all.

The following examples are submitted to exemplify the process of the instant invention and are not intended to limit the scope of the invention.

EXAMPLE 1

The reactor comprised a one-liter titanium autoclave reactor equipped with an air/nitrogen feed system, a condenser and reflux line, a vent-gas system, on-line gas chromatographic analyzers, a reactor heating and cooling system, in-place temperature measurement sensors, and a tail-out catalyst/semicontinuous addition system. Into the reactor, there was added 20.25g of cobaltous acetate, $Co(C_2H_3O_2)\cdot 4H_2O$, 30.04g water, 400 ml (420g) glacial acetic acid, 20.10g cyclohexanone and 40g cyclohexane. An additional 30.11g of cyclohexane was added during the reaction in a simulation of a semi-continuous procedure for a total of 70.11g of cyclohexane An additional 50 ml(52.5g) glacial acetic acid was added during the period of the oxidation reaction because 30.11g of cyclohexane was added during the reaction. Total pressure was 1020 psig. Oxygen pressure was 204 psig. Temperatures at the beginning of the run was 95° C. (203° F.) After 19 minutes, reaction temperature began rising to 96° C. (205° F.). Reactor temperature was reduced to 95° C (203° F) by reducing heat input into the reactor After 77 minutes, oxygen vent gas rose to above 12(vol) %, indicating the oxidation of cyclohexane to adipic acid was complete The reactor was cooled, depressurized, and the reaction mixture was withdrawn from the reaction zone After removal of the catalyst by extraction with acetone, the organic residue was treated to recover the reaction products as described earlier Identifiable products by gas chromatographic analysis are given in Table I Yield of adipic acid was 75.6(mol) %.

EXAMPLE 2

In the procedure of Example I, the oxidation of cyclohexane was repeated in a simulated semi-continuous procedure but with the addition of 3.2 g of hydrobromic acid to determine if the presence of bromine as a catalyst component improved yield of adipic acid Yield of adipic acid was 37.8(mol) %. Details are in Table I.

EXAMPLE 3

The procedure of Example I was repeated as a batch procedure but methyl ethyl ketone was added as the initiator instead of cyclohexanone. As a batch procedure, 400 ml, 420g, acetic acid was added at the initiation of the run with the other feed components. Yield of adipic acid was 82.6(mol) %. Details are in Table II.

EXAMPLE 4

The procedure of Example 3 was repeated as a batch procedure but with the addition of 18g of manganese acetate. The amount of cobalt acetate was reduced to 1.8g. Almost no reaction occurred. Details are in Table II.

EXAMPLE 5

The procedure of Example 4 was repeated as a batch procedure but with the addition of sodium acetate. Almost no reaction occurred Details are in Table II.

EXAMPLE 6

The procedure of Example I was repeated as a batch procedure using 400 ml, 420g of glacial acetic acid as a component of the initial feed mixture Water was not added to the reaction mixture until 10 minutes after the beginning of the run when oxygen absorption had begun and carbon oxides began to be produced. At the start of the run, the reactor temperature was 95° C. (203° F.). After 8 minutes, the initial rector temperature began to rise rapidly reaching 110° C. (229° F.) in 10 minutes with evolution of carbon oxides. The addition of water to the reaction mixture was begun at that time and completed in 4 minutes. A total of 30 ml of water was added after the oxidation of the cyclohexane to adipic acid had begun. Reaction temperature was reduced to 95° C. (203° F.) by reducing heat input After 64 minutes, oxygen vent gas rose to 12 (vol) %, indicating the oxidation of cyclohexane to adipic acid was complete Yield of adipic acid was 86(mol) % . Details are in Table III.

EXAMPLE 7

The procedure of Example 6 was repeated as a batch procedure using 400 ml, 420g, of glacial acetic acid. Water was not added until 21 minutes after the beginning of the run when oxygen absorption had begun, carbon oxides had begun to be produced and reactor temperature had increased. At the start of the run, reactor temperature was 95° C. (203° F.). At 7 minutes into the run, reactor temperature began to rise. An increase in cooling of the reactor by external means was ineffective. At 9 minutes into the run, reactor temperature had reached 106° C. (223° F.). Reduction of heat to 95° C. (203° F.) was obtained by removing at 11 minutes the outside source of heat. Carbon oxide production was detected at 10 minutes. Water, 30.10g, was added to the reaction mixture at 21 minutes. At 67 minutes, oxygen vent gas rose to 12(vol) %, indicating the oxidation of cyclohexane was complete. Yield of adipic acid was determined by gas chromatographic analysis Yield of adipic acid, an average of two analyses, was 88(mol) %. Details are in Table III.

EXAMPLE 8

The procedure of Example 7 was repeated but no water was added at all. Cyclohexanone was added to the reaction mixture to determine the utility of cyclohexanone as an initiator in the absence of water. Yield of adipic acid was 80(mol) %. Details are in Table III.

TABLE I

Comparison of Co and Co/Br Catalysts

| Example | 1 | 2 |
|---|---|---|
| Reaction Conditions | | |
| Starting Materials: | | |
| Cyclohexane | 70 g | 70 g |
| Acetic Acid-Glacial | | |
| Initial | 420 g | 420 g |
| Added | 52.5 g | 52.5 g |
| Co(OAc)$_2$.4H$_2$O | 20 g | 20 g |
| Water | 30 g | 30 g |
| HBr | — | 3.2 g |
| Cyclohexanone | 20 g | 20 g |
| Temperature | 95° C. | 95° C. |
| Pressure | | |
| Total | 1020 psig | 1020 psig |
| O$_2$ Partial | 204 psig | 204 psig |
| Time | | |
| Cyclohexane Oxidation Began | 19 min. | 7 min. |
| Oxidation Period | 77 min. | 37 min. |
| Results | | |
| Identifiable Products - Yield (mol), (M/M) % | | |
| Cyclohexane | 10% | 40% |
| Cyclohexanone, Cyclohexanol | 6.6% | 14% |
| Succinic Acid | — | 6.8% |
| Glutaric Acid | 7.2% | 2.0% |
| Adipic Acid | 75.6% | 37.8% |
| Conversion To Adipic Acid | 90% | 60% |
| Selectivity To Adipic Acid | 84% | 63% |

TABLE II

Comparison of Co and Co/Br Catalysts Catalysts, Alone and With Added Acetate Ion

| Example | 3 | 4 | 5 |
|---|---|---|---|
| Reaction Conditions | | | |
| Starting Materials | | | |
| Cyclohexane | 70 g | 70 g | 70 g |
| Acetic Acid - Glacial | 420 g | 420 g | 420 g |
| Co(OAc)$_2$.H$_2$O | 20 g | 1.8 g | 1.8 g |
| Mn(OAc)$_2$.4H$_2$O | — | 18 g | 18 g |
| Water | 30 g | 30 g | 30 g |
| NaOAc | — | — | 4.5 |
| MEK | 15 g | 15 g | 15 g |
| Temperature | 95° C. | 95° C. | 95° C. |
| Pressure | | | |
| Total | 1020 psig | 1030 psig | 1030 psig |
| O$_2$ Partial | 206 psig | 206 psig | 206 psig |
| Time | | | |
| Cyclohexane Oxidation Began | 104 min. | 300+ min. | 300+ |
| Oxidation Period | 89 min. | — | — |
| Results | | | |
| Identifiable Products - Yield (mol) %, (M/M) % | | | |
| Cyclohexane | 4.1% | 98% | 98% |
| Cyclohexanone, Cyclohexanol | 5.6% | 2% | 2% |
| Glutaric Acid | 7.7% | — | — |
| Adipic Acid | 82.6% | — | — |
| Conversion To Adipic Acid | 96% | 2% | 2% |
| Selectivity To Adipic Acid | 86% | 0% | 0% |

TABLE III

Effect of Adding Water at Different Times During The Reaction

| Example | 1 | 6 | 7 | 8 |
|---|---|---|---|---|
| Reaction Conditions | | | | |
| Starting Materials: | | | | |
| Cyclohexane | 70 g | 70 g | 70 g | 70 g |
| Acetic Acid - Glacial | | | | |
| Initial | 420 g | 420 g | 420 g | 470 g |
| Added | 52.5 | — | — | — |
| Co(OAc)$_2$.4H$_2$O | 20 g | 20 g | 20 g | 20 g |
| Cyclohexanone | 20 g | 20 g | 20 g | 20 g |
| Water Added: | | | | |
| Amount | 30 g | 30 g | 30 g | — |
| Time | 0 min. | 10 min. | 21 min. | — |
| Temperature | 95° C. | 95° C. | 95° C. | 95° C. |
| Pressure | | | | |
| Total | 1020 psig | 1030 psig | 1030 psig | 1030 psig |
| O$_2$ Partial | 204 psig | 206 psig | 206 psig | 206 psig |
| Time | | | | |

TABLE III-continued

Effect of Adding Water at Different Times During The Reaction

| Example | 1 | 6 | 7 | 8 |
|---|---|---|---|---|
| Cyclohexane Oxidation Began | 19 min. | 8 min. | 7 min. | 7 min. |
| Oxidation Period | 77 min. | 64 min. | 67 min. | 65 min. |
| Results | | | | |
| Identifiable Products - | | | | |
| Yield (mol), (M/M)% | | | | 5.3% |
| Cyclohexane | 10% | 2.5% | 1.65%** | |
| Cyclohexanone, | | | | 4.5% |
| Cyclohexanol | 6.6% | 4.9% | 5.25%** | 10% |
| Glutaric Acid | 7.2% | 6.8% | 5.7%** | 80% |
| Adipic Acid | 76% | 86% | 88%** | |
| Conversion To Adipic Acid | 90% | 98% | 98% | 95% |
| Selectivity To Adipic Acid | 84% | 88% | 90%** | 84% |

**Average of two analyses

That which is claimed is:

1. A process for the manufacture of adipic acid wherein cyclohexane is oxidized with a source of oxygen in an aliphatic monobasic acid solvent having 2 to 8 carbon atoms in a presence of a soluble cobalt salt and in the presence of an initiation agent wherein said initiation agent is present in an amount of from about 0.1 to about 50 weight percent of said cyclohexane feedstock, wherein water is present only after the initiation of oxidation of said cyclohexane, wherein said water is present in an amount which does not exceed 50 weight percent of the cyclohexane present and wherein the reaction is conducted at a temperature of about 50° C. to about 150° C. at an oxygen partial pressure of about 50 to about 420 pounds per square inch absolute 2. The process of claim 1 wherein said water present in the oxidation of cyclohexane is added as a single charge, or intermittently as a series of additions, after the initiation of oxidation of said cyclohexane.

3. The process of claim 1 wherein the amount of water is in the range of about 1 to about 10 weight percent based on the weight of the aliphatic monobasic acid solvent and the water is added when the mole ratio of oxygen absorbed to cyclohexane present is about 1:1.

4. The process of claim 1 wherein about 10 to about 1000 millimols of cobalt are present per mol of cyclohexane feedstock.

5. The process of claim 1 wherein the temperature is in the range of about 50° C. to about 150° C.

6. The process of claim 1 wherein the source of oxygen is air and the partial pressure of air is in the range of about 715 to about 2000 pounds per square inch absolute.

7. The process of claim 1 wherein the aliphatic monocarboxylic acid has from two to four carbon atoms.

8. The process of claim 1 wherein the aliphatic monocarboxylic acid is acetic acid 9. The process of claim 1 wherein the weight ratio of acetic acid to cyclohexane is about 0.7 to about 14.

10. The process of claim 1 wherein an oxygen containing aliphatic hydrocarbon initiation agent is used.

11. The process of claim 1 wherein said initiation agent is selected from the group consisting of cyclohexanone and a mixture of cyclohexanone and cyclohexanol.

12. The process of claim 1 wherein the initiation agent is acetaldehyde.

13. The process of claim 1 wherein the induction agent is methyl ethyl ketone.

14. The process of claim 1 wherein the initiation of said oxidation of cyclohexane is detected using a suitable means, and wherein said suitable means of detection of said oxidation of said cyclohexane comprises a means of measurement of rapid changes in reaction temperatures.

15. The process of claim 1 wherein the initiation of said oxidation of cyclohexane is detected using a suitable means, and wherein said suitable means of detection of said oxidation of said cyclohexane comprises a means of measurement of increases in oxygen absorption.

16. The process of claim 1 wherein the initiation of said oxidation of cyclohexane is detected using a suitable means, and wherein said suitable means of detection of said oxidation of said cyclohexane comprises a means of measurement of production of carbon oxides.

* * * * *

UNITED STATES PATENT AND TRADEMARK OFFICE
CERTIFICATE OF CORRECTION

PATENT NO. : 5,221,800
DATED : June 22, 1993
INVENTOR(S) : Chang-Man Park, et al It is certified that error appears in the above-indentified patent and that said Letters Patent is hereby corrected as shown below:

| Col. | Line | |
|---|---|---|
| 3 | 60 | "oxidation Q reaction" should read --oxidation reaction--. |
| 5 | 33-4 | "manganese has Q on the oxidation" should read --manganese has on the oxidation--. |
| 5 | 62 | "However, Q in Example 1" should read --However, in Example 1--. |

Signed and Sealed this

Twenty-seventh Day of February, 1996

Attest:

BRUCE LEHMAN

Attesting Officer

Commissioner of Patents and Trademarks